(12) United States Patent
Segrell

(10) Patent No.: US 8,735,382 B2
(45) Date of Patent: May 27, 2014

(54) INFUSION AND INJECTION SOLUTION OF LEVODOPA

(75) Inventor: Nil Dizdar Segrell, Linköping (SE)

(73) Assignee: Dizlin Medical Design AB, Vastervik (SE)

( * ) Notice: Subject to any disclaimer, the term of this patent is extended or adjusted under 35 U.S.C. 154(b) by 0 days.

(21) Appl. No.: 13/208,628

(22) Filed: Aug. 12, 2011

(65) Prior Publication Data

US 2011/0294889 A1 Dec. 1, 2011

Related U.S. Application Data

(63) Continuation of application No. 11/631,602, filed as application No. PCT/SE2005/001135 on Jul. 8, 2005, now abandoned.

(30) Foreign Application Priority Data

Jul. 12, 2004 (SE) ...................................... 0401842

(51) Int. Cl.
*A01N 43/00* (2006.01)
*A61K 31/33* (2006.01)

(52) U.S. Cl.
USPC .......................................... 514/183; 514/567

(58) Field of Classification Search
None
See application file for complete search history.

(56) References Cited

U.S. PATENT DOCUMENTS

| | | | |
|---|---|---|---|
| 3,911,137 A | 10/1975 | Miki et al. | |
| 3,916,004 A | 10/1975 | Okada et al. | |
| 4,409,233 A | 10/1983 | Tsukada et al. | |
| 4,850,980 A * | 7/1989 | Lentz et al. | 604/248 |
| 5,880,124 A | 3/1999 | Gross | |
| 6,387,936 B1 | 5/2002 | Blanchard-Bregeon et al. | |

FOREIGN PATENT DOCUMENTS

| | | |
|---|---|---|
| CA | 2513077 A | 7/2005 |
| EP | 252290 A2 | 1/1988 |
| EP | 451484 A1 | 10/1991 |
| EP | 610595 A2 | 8/1994 |
| JP | 54-105221 A | 8/1979 |
| JP | 10-226646 A | 8/1998 |
| SE | 512655 C2 | 4/2000 |
| WO | 95/13803 A | 5/1995 |
| WO | 99/55336 A | 11/1999 |
| WO | 01/01984 A1 | 1/2001 |
| WO | 2004/056306 A2 | 7/2004 |
| WO | 2005/023185 A2 | 3/2005 |

OTHER PUBLICATIONS

Biomedical Engineering Guide, 1999, Baxa Corporation.*
STN Accession No. 1980:64767 CAPLUS.*
Hauser, Neurology, Jan. 13, 2004 vol. 62, No. 1, suppl. 1 S64-S71.*
Bredberg et al, "Intraduodenal infusion of a water-based levodopa dispersion for optimization of the therapeutic effect in severe Parkinson's disease", European Journal of Clinical Pharmocology, 45:117-122 (1993).
Kankkumen et al, "Improved stability and release control of levodopa and metaraminol using ion-exchange fibers and transdermal iontophonresis", European Journal of Pharmaceutical Sciences, 16:273-280 (2002).
Bredberg et al, "Pharmacokinetics of levodopa and carbidopa in rats following different routes of administration", Pharmaceutical Research, 11(4):549-555 (1994).
Wood, Editor, Donald Calne, "Treatment of Parkinson's Disease", The New England Journal of Medicine, 392 (14):1021-1027 (1993).
Chan, "Importance of within subject variation in lovodopa pharmacokinetics: a 4 year cohort study in Parkinson's disease", Journal of Pharmacokinetic and Pharmacodynamics, 32(3-4):307-331 (2005), Abstract only.
D.J. Stennett, et al., "Stability of levodopa in 5% dextrose injection at pH 5 or 6", American Journal of Hospital Pharmacy, 43: 1726-1728 (Jul. 1986).
Weintraub M. et al: "IV levodopa preparation and sterilization by filtration", Hospital Formulary, 20: 926-930 (Aug. 1985).
Lullman et al: "Color Atlas of Pharmacology, 2nd edition", Stuttgart: Thieme, pp. 188-189 (2000).
C.G. Goetz, et al "Intravenous levodopa in hallucinating Parkinson's disease patients: High-dose challenge does not precipitate hallucinations", Neurology, 50: 515-517 (1998).
Olanow, "Levodopa/Dopamine Replacement Strategies in Parkinson's Disease—Future Directions", Movement Disorders, 23(1):S613-S622 (2008).
Kao et al, Pharmaceutical Research, 17:978-984 (2000).
"Drugs in Japan", edited by Japan Pharmaceutical Information Center, Oct. 25, 2003, pp. 2449-2455.
Official Action dated Feb. 18, 2014 from corresponding Japanese Application No. 2012-183865.
English Translation of of Official Action dated Feb. 18, 2014 from corresponding Japanese Application No. 2012-183865.

* cited by examiner

*Primary Examiner* — Brandon Fetterolf
*Assistant Examiner* — Jean Cornet
(74) *Attorney, Agent, or Firm* — Porter Wright Morris & Arthur LLP

(57) ABSTRACT

An infusion or injection solution of Levodopa containing at least 10 mg/mL of Levodopa, or at least 5 mg/mL of Levodopa together with at least 0.5 mg/mL of at least one inhibitor of a Levodopa-metabolising enzyme is disclosed. The solution further contains a buffer, a physiologically acceptable sugar, such as glucose, a physiologically acceptable acid, such as hydrochloric acid, and optionally a stabilizer, and has a pH of lower than or equal to 6. There are also described a disposable syringe containing an infusion or injection solution of Levodopa, optionally together with a Levodopa-metabolising enzyme, and an infusion pump cassette containing an infusion or injection solution of Levodopa optionally together with a Levodopa-metabolising enzyme.

29 Claims, No Drawings

INFUSION AND INJECTION SOLUTION OF LEVODOPA

RELATED APPLICATIONS

The present application is a continuation of U.S. application Ser. No. 11/631,602 filed Jan. 2, 2008, now abandoned which is a 371 of PCT/SE2005/001135 filed Jul. 8, 2005.

FIELD OF THE INVENTION

The present invention relates to an infusion or injection solution of Levodopa which optionally comprises at least one inhibitor of a Levodopa-metabolising enzyme. The invention also relates to a disposable syringe as well as an infusion pump cassette containing a therapeutically effective amount of an infusion or injection solution of Levodopa, optionally further containing at least one inhibitor of a Levodopa-metabolising enzyme.

BACKGROUND

Parkinson's Disease (PD) is very common and is contracted by approximately 15 out of 10,000 people in the Western world. The age of debut is usually between 55 and 60 years. The disease is characterised by rigidity and tremors caused by a massive loss of nigrostratial neurones and subsequently a lack of dopamine [3,4-dihydroxyphenylethylamine] (1). The symptoms of Parkinson's Disease appear upon a loss of approximately 80% of dopamine neurones.

Tyrosine hydroxylase is the enzyme which transforms tyrosine into Levodopa [Levodopa=3-(3,4-dihydroxiphenyl)-L-alanine] (2), which then is metabolised into dopamine by dopadecarboxylase (DDC) both in the brain and in the peripheral circulation. Dopamine is metabolised into 3,4-dihydroxyphenylacetic acid (DOPAC), 3-methoxytyramine and Homovanilic acid (HVA) by the two enzymes monoamino oxidase (MAO) and catechol-o-methyltransferase (COMT) (3).

Levodopa is still the most important treatment for Parkinson's disease and intermittent oral Levodopa treatment achieves good relief of the symptoms at early stages of the disease. In spite of the massive loss of neurones there still is an adequate storage capacity, which makes possible an even release of dopamine into the synaptic spatium during interval dosage. Levodopa given orally is, however, metabolised to 90% in the first passage before reaching the brain. Bioavailability can be increased by simultaneous administration of DDC-inhibitors, such as carbidopa [L-2-hydrazino-3-(3,4-dihydroxyphenyl)-2-methylpropanoic acid] or benserazide [2-amino-3-hydroxy-N'-(2,3,4-trihydroxybenzyl) propionohydrazide], which both compete with Levodopa for the metabolising DDC- and thus allow more of the administered Levodopa to reach the brain before it is metabolised into dopamine.

Levodopa is a neutral amino acid, which must pass the blood-brain barrier before it reaches the central nervous system. This transport is energy consuming. The half-life of Levodopa is short, 30 to 60 minutes. Under the influence of the enzyme dopadecarboxylase (DDC), the greater part of Levodopa is metabolised into dopamine. This enzyme is found in a number of organs but above all in muscles, red blood cells and in the skin where it is an important component in the formation of melanin pigment (5). Upon the intake of Levodopa alone, more than 90% is metabolised before it reaches the brain (6).

In order to increase the bioavailability of Levodopa, and reduce its secondary effects on the system, Levodopa is therefore given in combination with a decarboxylase inhibitor (benserazide or carbidopa) in the same oral dosage form. In both the intestine and the blood-brain barrier Levodopa has to compete for the enzyme transport with other amino acids from, for example, protein-rich meals (7). The absorption of Levodopa takes place primarily in the proximal third part of the small intestine (8). Variations in the emptying of the ventricle can, therefore, result in large variations in the serum concentration in the same patient despite intake of the same amount of Levodopa. The inhibition of dopadecarboxylase does not, however, increase the half-life for Levodopa very greatly, which points to the metabolising of Levodopa being shunted to the smaller COMT pathway. This leads to the formation of the metabolite 3-0-methyldopa (OMD) which because of its long half-life (9) is accumulated in plasma and reaches manifestly higher levels as compared to Levodopa (10). The metabolite OMD is also a neutral amino acid and can therefore compete with Levodopa for the passage over the two barriers.

Pharmacokinetic and pharmacodynamic problems concerning Levodopa treatment arise after approximately five years of treatment in the form of fluctuations—from dyskinesia (involuntary movements) to akinesia (totally inhibited movements). When clinical fluctuations begin a distinct parallel can be seen between the decreasing plasma concentrations and the declining clinical response to the Levodopa dose administered. Yet, at an advanced stage in the disease rapid "on-off" fluctuations can be seen without any visible relation to the plasma concentration of Levodopa. This can be explained by there being a certain delay of about 90 minutes in the concentration levels between plasma and the central nervous system (CNS), where the CNS concentration is directly correlated to clinical status.

After suffering from the disease for 5-10 years, the storage capacity of the patient has, however, decreased somewhat due to the continuous loss of neurones, and "wearing off" problems occur. At this stage the storage capacity for dopamine is not adequate until the next dose is due, and Levodopa must therefore be administered at shorter intervals.

At a later stage of the disease, fluctuations occur too with both dyskinesia and bradykinesia (partially inhibited movements) in spite of increasingly frequent doses of dopamine, and sometimes seemingly with no relation to the intake of medicine. This is assumed to be caused by hypersensitivity of the postsynaptic dopamine receptors, resulting in a narrowing of the therapeutic window. This entails a much smaller difference between effective dose and overdose.

Levodopa belongs to the group of neutral amino acids and is absorbed by oral administration only in the proximal third of the small intestine via competitive active transport. It has been shown that approximately 10% of the total dose enters the blood circulation. By avoiding protein-rich meals during the daytime, and in close proximity to the individual times of dosage, it is possible to facilitate Levodopa absorption from the intestine and to a certain degree relieve clinical fluctuations. There is not always a direct correlation between the serum concentration of Levodopa and clinical fluctuations. This is probably due to the fact that the passage over the blood-brain barrier also takes place through active transport and even there competes with other neutral amino acids. An overview of the analysis methods for Levodopa has been published (11)

Experimentally it has been possible to show in animals that hypersensitivity of the postsynaptic dopamine receptors takes place upon interval stimulation, as well as it being possible to achieve hyposensitivity with continuous stimulation of these receptors with Levodopa. Such treatment of human patients should bring about a widening of the therapeutic window and a decrease in the clinical fluctuations (12), a treatment strategy that has not been possible, due to the insolubility of Levodopa in aqueous solutions at approximately neutral pH.

Oral dosage forms of Levodopa for treatment of Parkinson's disease have been used since the 1960ies and the progress of the disease and the treatment thereof follows the description above. In order to improve the treatment of the patients new treatment approaches have been developed such as dopamine agonists and enzyme inhibitors. However, these have not been able to solve all the problems encountered with the traditional Levodopa treatment.

A new Levodopa formulation comprising carbidopa in the form of a viscous gel, Duodopa®, has recently become available from NeoPharma AB, Uppsala, Sweden, for treatment of Parkinson's disease. This treatment is given directly to the duodenum with a nasoduodenal probe or with a percutaneous probe. With this system a continuous administration of Levodopa is possible but the limitations of the gastric transport barrier remains.

There are at present no commercially available pharmaceutical preparations for intravenous, subcutaneous or intrathekal administration due to the poor solubility of Levodopa at neutral pH. Large quantities of Levodopa-containing liquid would be required to give a therapeutic effect at a near neutral pH, and further, Levodopa auto-oxidises rapidly. However, the Swedish patent 512 655 describes the preparation of a Levodopa infusion solution containing 5 mg/mL Levodopa as the only active ingredient. The Levodopa is dissolved in HCl and diluted with glucose, but at higher concentrations than 5 mg/mL the Levodopa precipitates. For a daily dosage of e.g. 600 mg Levodopa, a patient would need 120 mL of said infusion solution per day. It would be desirable to have an infusion solution or injection solution that is therapeutically effective in lower daily volumes.

DESCRIPTION OF THE INVENTION

The present invention provides an infusion or injection solution that is therapeutically effective in lower daily volumes. This is achieved by first dissolving the Levodopa in a physiologically acceptable acid and then adding an organic buffer and small portions of a physiologically acceptable sugar, such as glucose, at a time, ensuring that no precipitation of Levodopa occurs. The higher the concentration of Levodopa in the solution, the more slowly the addition of a sugar solution should be.

As mentioned in the background, the bioavailability of Levodopa can be increased by simultaneous administration of an inhibitor of a Levodopa-metabolising enzyme. Therefore, the concentration of Levodopa in the infusion or injection solution of the invention can be as low as 5 mg/mL of Levodopa as long as the solution also comprises at least 0.5 mg/mL of at least one inhibitor of a Levodopa-metabolising enzyme.

Thus, the present invention is directed to an infusion or injection solution of Levodopa containing
a1) at least 10 mg/mL of Levodopa, or
a2) at least 5 mg/mL of Levodopa together with at least 0.5 mg/mL of at least one inhibitor of a Levodopa-metabolising enzyme,
b) a buffer,
c) a physiologically acceptable sugar, and
d) a physiologically acceptable acid,
the pH of the solution being lower than or equal to 6.

Thus, when a solution containing 10 mg/mL of Levodopa according to the invention is administered to a patient requiring 600 mg Levodopa per day, the total volume can be cut into half compared to the prior art 5 mg/mL of Levodopa solution, resulting in a daily volume of only 60 mL. This reduction in volume will enable the use of smaller infusion pump cassettes—or alternatively larger doses in the cassettes. The same applies for other administration means, such as syringes.

Examples of the buffer in the solution of the invention are 2-amino-2-hydroxymethyl-1,3-propane diol (Trometamol) and tris(hydroxymethyl)aminomethane (Tris).

In an embodiment of the invention the solution further comprises a stabilizer, such as sodium pyrosulphite, In a preferred embodiment of the invention, the volume of the solution is adapted for a single or continuous intravenous and/or subcutaneous and/or intrathekal administration. Currently, in addition to traditional needles, infusion pumps are used for administration of solutions to patients, and these are also possible to use with the infusion or injection solution of Levodopa of the invention.

In current studies the PCA pump CADD system from Smiths Medical Sverige AB, Sollentuna, Sweden, is used for administering the Levodopa infusion solution according to the invention. This system can be used both for infusion with the infusion solution in cassettes (maximum 100 mL) and with the infusion solution in a bottle connected with an adapter to the pump system. For subcutaneous infusion the Disetronic pump system from Disetronic Medical Systems AB, Sweden, can be used. The advantage with this system is the small size of the pump and the possibilities using it during different activities without interference. Maximum infusion solution is 20 mL. For intrathekal infusion the Medtronic pump system from Medtronic AB, Järfälla, Sweden, can be used. The pump is placed subcutaneously and refilled regularly by medical staff.

In another embodiment of the invention the physiologically acceptable sugar is selected from dextran, e.g. dextran 70, 60 or 40, mannitol and glucose, and glucose is presently preferred.

In yet another embodiment, the pH of the infusion or injection solution of the invention is in the range of 3 to 6.

In a further embodiment of the invention the amount of Levodopa in a2) is selected from the range 5 mg/mL to 25 mg/mL and the amount of the inhibitor of a Levodopa-metabolising enzyme is selected from the range 0.5 mg/mL to 6.25 mg/mL.

In still another embodiment of the invention, the inhibitor of a Levodopa-metabolising enzyme in the infusion or injection solution is selected from the group consisting of dopa decarboxylase (DDC) inhibitors, catechol-o-methyltransferase (COMT) inhibitors, and enzymes monoamino oxidase (MAO-B) inhibitors.

In a preferred embodiment the DDC-inhibitor is L-2-hydrazino-3-(3,4-dihydroxy-phenyl)-2-methylpropanoic acid (carbidopa) or 2-amino-3-hydroxy-N'-(2,3,4-trihydroxybenzyl) propionohydrazide (benserazide).

In another preferred embodiment the COMT inhibitor is (E)-2-cyano-3-(3,4-dihydroxy-5-nitrophenyl)-N,N-diethyl-2-propane amide (entacapone).

In yet another preferred embodiment the MAO-B inhibitor is (R)-N,α-dimethyl-N-(2-propynyl)phenethyl amine (selegiline).

The physiologically acceptable acid comprised by a preferred infusion or injection solution of Levodopa according to the invention is hydrochloric acid or acetic acid.

Acid solutions are often used for intravenous infusion. pH below 3 is known to give vessel irritations and trombophlebitis. Glucose solutions can however have a low pH (3.5) without any side effects. Weak acids as hydrochloric acid and acetic acid are tolerated for intravenous infusion in pH above 3. Levodopa is easily soluble at low pH. However it is crystallized at higher pH although the crystallization doesn't appear instantly.

Another aspect of the invention is directed to a disposable syringe containing a therapeutically effective amount of an infusion or injection solution of Levodopa dissolved in a physiologically acceptable acid, containing a buffer and a physiologically acceptable sugar and having a pH of lower than or equal to 6. The therapeutically effective amount is decided empirically based on the condition of the patient, or a standard dose is recommended by the manufacturer, and it is preferably made up of a solution having a concentration of at least 10 mg/mL of Levodopa, and the physiologically acceptable sugar is preferably selected from dextran, e.g. dextran 70, 60 or 40, mannitol or glucose, preferably glucose, and the solution having a pH of lower than or equal to 6, is preferably a solution having a pH in the range of 3 to 6.

In an alternative embodiment of this aspect of the invention the infusion or injection solution in the disposable syringe further comprises at least one inhibitor of a Levodopa-metabolising enzyme in an amount that together with an amount of Levodopa gives a therapeutically effective amount of the solution. In this case, the therapeutically effective amount is preferably made up of a solution having at least 5 mg/mL of Levodopa together with at least 0.5 mg/mL of at least one inhibitor of a Levodopa-metabolising enzyme, such as Levodopa in the range of 5 mg/mL to 25 mg/mL and the amount of inhibitor(s) of a Levodopa-metabolising enzyme in the range 0.5 mg/mL to 6.25 mg/mL.

A syringe of the invention will typically hold 1 to 10 mL of an infusion or injection solution according to the invention. Still another aspect of the invention is directed to an infusion pump cassette containing a therapeutically effective amount of an infusion or injection solution of Levodopa, dissolved in a physiologically acceptable acid, containing a buffer, a physiologically acceptable sugar, and having a pH of lower than or equal to 6. The therapeutically effective amount is decided empirically based on the condition of the patient, or a standard dose is recommended by the manufacturer, and it is preferably made up of a solution having a concentration of at least 10 mg/mL of Levodopa, and the physiologically acceptable sugar is preferably selected from dextran, e.g. dextran 70, 60 or 40, mannitol or glucose, preferably glucose, and the solution having a pH of lower than or equal to 6, is preferably a solution having a pH in the range of 3 to 6.

In an alternative embodiment of this aspect of the invention the infusion pump cassette further comprises at least one inhibitor of a Levodopa-metabolising enzyme in an amount that together with an amount of Levodopa gives a therapeutically effective amount of the solution. In this case, the therapeutically effective amount is preferably made up of a solution having at least 5 mg/mL of Levodopa together with at least 0.5 mg/mL of at least one inhibitor of a Levodopa-metabolising enzyme, such as Levodopa in the range of 5 mg/mL to 25 mg/mL and the amount of inhibitor(s) of a Levodopa-metabolising enzyme in the range 0.5 mg/mL to 6.25 mg/mL.

The size and shape of the cassette will vary depending on the actual infusion pump system that will be used for the administration of the infusion or injection solution of the invention.

The invention will now be illustrated by description of examples of the preparation of the infusion or injection solution and use thereof, but it should be understood that the disclosures are not intended to limit the scope of the invention.

Highly Concentrated Levodopa Solutions Optionally Containing Carbidopa

Addex®-Tham that is used in the preparation of the infusion solutions, is a concentrated infusion solution sold by Fresenius Kabi AB, Uppsala Sweden. The active ingredient is Trometamol, 2-amino-2-hydroximetylpropan-1,3-diol (Tris-Hydroximetyl-Amino-Metan), also named TRIS or THAM, and it is an organic buffer. THAM functions as a proton acceptor, i.e. a weak base.

Stock Solution 1 of Levodopa 100 mg/mL
Levodopa 10 g
HCl 1 mole/L 31 g
Sodium pyrosulfite 1 g
Water for injection add to 100 mL The Levodopa is dissolved in the HCl solution in a 100 mL flask. The sodium pyrosulfite is weighed into a 10 mL injection vial and 2 mL of sterile water is added for dissolution. Water in an amount of 50 mL is added to the flask containing Levodopa, followed by addition of the sodium pyrosulfite solution. The mixture is poured into a 100 mL measuring flask and water for injection is added up to the 100 mL mark. The resulting solution is sterile filtered into a 100 mL injection flask. A Sterivex GV-filter 0.22 μm was used.

Levodopa 10 mg/mL—Solution
Levodopa, 40 mL of the 100 mg/mL stock solution 1
Addex-Tham 5.5-6 mL
Glucose 50 mg/mL add to 200 mL Addex-Tham was added to the Levodopa solution. Glucose, 50 mg/mL, was added slowly in portions of approximately 10 mL with stirring up to a total volume of 200 mL. The pH of the solution was 3.5-4 and the shelf-life was >3 days.

Stock Solution 2 of Levodopa 50 mg/mL+Carbidopa
Levodopa 5 g
Carbidopa 0.5 g
HCl 1 mole/L 36 g
Sodium pyrosulfite 0.5 g
Water for injection add to 100 mL The Levodopa is dissolved in the HCl solution in a 100 mL flask. The sodium pyrosulfite is weighed into a 10 mL injection vial and 2 mL of sterile water is added for dissolution. Water in an amount of 50 mL is added to the flask containing Levodopa, followed by addition of the sodium pyrosulfite solution. The mixture is poured into a 100 mL measuring flask and water for injection is added up to the 100 mL mark. The resulting solution is sterile filtered into a 100 mL injection flask. A Sterivex GV-filter 0.22 μm was used.

Levodopa 5 mg/mL—Solution Containing Carbidopa 0.5 mg/mL
Levodopa, 20 mL of the 50 mg/mL stock solution 2
Addex-Tham 3 mL
Glucose 50 mg/mL add to 200 mL Addex-Tham was added to the Levodopa solution. Glucose, 50 mg/mL, was added up to a total volume of 200 mL. The pH of the solution was 3.5-4 and the shelf-life was >3 days.

Levodopa 10 mg/mL—Solution Containing Carbidopa 1 mg/mL
Levodopa 40 mL of the 50 mg/mL stock solution 2
Addex-Tham 5.5-6 mL
Glucose 50 mg/mL add to 200 mL Addex-Tham was added to the Levodopa stock solution 2. Glucose, 50 mg/mL, was added slowly in portions of approximately 10 mL with stirring up to a total volume of 200 mL. The pH of the solution was 3.5-4 and the shelf-life was >3 days.

Experiments with Levodopa Solutions of the Invention

Solubility

Levodopa can be dissolved in HCl up to 100 mg/mL without any precipitation. To raise the pH with glucose in a way according to the invention and still get a stabile solution, it is possible to obtain 10 mg/mL Levodopa, and with 2 mg/mL Carbidopa addition 20 mg/mL Levodopa. A precipitate appears at 30 mg/mL Levodopa in the presence of 3 mg/mL Carbidopa.

Preparation of Levodopa Solution

The steps of producing the solutions of the invention are made rather quickly up to the addition of glucose. Initially, approximately half of the volume of the glucose solution is added, followed by a drop by drop addition of the rest of the volume at approximately 10 min intervals and constant stirring until the pH is acceptable (e.g. pH 3-6).

Stability

A solution of 5 mg/mL Levodopa and 0.5 mg Carbidopa has been heated to 60° C. and left to stand for 36 hours, and then at room temperature for 1 week, without any sign of discoloration or precipitation.

Mannitol Compared to Glucose

Mannitol can be used instead of glucose in the Levodopa solutions of the invention, but it is much more unstable and a precipitate is formed in a few hours.

Different Applications of the Infusion Solution of the Invention

Previously, individual studies have shown that fluctuations with alternating dyskinesia and bradykinesia decline and can even disappear during on-going treatment by oral and intravenous levodopa administration (12). As yet, no studies exist on the long-term effects of continuous intravenous treatment with Levodopa with prior art solutions. Nor has the subsequent, traditional oral treatment need for Levodopa been investigated.

In preliminary studies we have now been able to show that both bradykinesia and above all dyskinesia decline during intravenous treatment with Levodopa and this effect remains even after five months. The patients have also been able to manage on reduced oral Levodopa treatment with lower doses and monotherapy.

Treatment Options

Intravenous Levodopa infusion or injection continuously or intermittently during 12 hours for 10 days is an effective treatment of clinical fluctuations. The effect is due to a widening of the therapeutic interval for Levodopa. The treatment has also a long-lasting effect of at least 5 months.

Infusion to subcutaneous tissue could avoid the appearance of clinical fluctuations both because of lower daily Levodopa dose and because of the continuous administration.

The method is very suitable for diagnostic intravenous Levodopa test. No other diagnostic method equal in merit is available.

A New Method for Levodopa Treatment

The Levodopa solutions according to the invention can be given as an infusion or injection into different tissues or to the blood. Several advantages can be seen:

Reduced volume compared to previously described Levodopa-solutions, due to a higher concentration of 10 mg/mL or from 5 mg/mL when the solution also contains at least one inhibitor of a Levodopa-metabolising enzyme in an amount of 0.5 mg/mL or more.

Prolonged durability of the effect with at least 5 months.

Addition of inhibitor of a Levodopa-metabolising enzyme is at a concentration of 0.5 mg/mL or more, such as dopadecarbolyxyase inhibitor, into the Levodopa solution which enables simultaneous administration of the two active ingredients to even an unconscious patient.

No interference from the gastric transport barrier.

Quick and simple regulation of the Levodopa concentrations by direct infusion or injection to blood or tissues.

Reduced post-treatment daily oral Levodopa dose, with a subsequent decrease of the risk of side effects.

Dynamic physiologic release of the signal substance dopamine by infusion or injection to tissues, which has similarities to the "normal" situation.

These advantages separate the use of the Levodopa solutions of the invention from prior art oral Levodopa preparations.

Another advantage is that the use of the Levodopa solutions of the invention doesn't need any surgical intervention since it can be given as an infusion through a standard needle (Venflon®), which is used for all types of intravenous infusions.

Infusion or injection to the subcutaneous tissue, of the abdomen, is given trough a needle of a syringe, which can be placed by the patient. The same infusion or injection method that is used for treatment with the dopamine agonist Apomorfin and for treatment with Insulin can be used with the infusion or injection solution of the invention.

The ease of self-administration of the Levodopa solutions of the invention by the patient from a syringe that can be carried by the patient as a disposable "emergency syringe" in case the patient senses that a condition with bradykinesia or akinesia is on its way, will help some patients to a more mobile life. In this case, the infusion or injection solution will possibly not need to contain the inhibitor of a Levodopa-metabolising enzyme. Therefore, the invention comprises a disposable syringe containing a therapeutically effective amount of an infusion or injection solution of Levodopa solved in a physiologically acceptable acid, containing a buffer, glucose and having a pH in the range of 3 to 6 and optionally further containing an inhibitor of a Levodopa-metabolising enzyme.

The Levodopa solution of the invention is significantly improved by the addition of at least one inhibitor of a Levodopa-metabolising enzyme, e.g. dopadecarbolyxyase inhibitor, into the solution. This simplifies the treatment and oral treatment with dopadecarbolyxyase inhibitor becomes unnecessary. The increased concentration of Levodopa decreases the volume necessary for infusion or injection of the daily Levodopa dose enabling the use of smaller infusion pump and a subsequent increased mobility for the patient. The treatment can be given both in ward and as policlinic treatment.

Thus, the Levodopa solutions of the invention can be delivered in ready-to-use cassettes adapted for the infusion pump used by the patient.

Test of a Patient's Therapeutic Response to Levodopa Treatment.

Parkinson's disease (PD) is diagnosed by clinical symptoms in combination with therapeutic response to treatment with Levodopa. Until now, only oral treatment has been provided to the patients. This means that the therapeutic response of the patient has been seen after a treatment period of 2-3 months. The therapeutic response is often discrete, and a certain positive effect is hard to evaluate, especially when the difference from day to day is very small.

The Levodopa solution of the invention, with or without the inhibitor of a Levodopa-metabolising enzyme, enables intravenous administration of Levodopa and makes it possible to register a positive response within one to two days!

The following test procedure may be used:
a. A predetermined dose of Levodopa is administered to the patient intravenously.
b. The dose is successively increased e.g. starting from 6 mL per hour and increasing by 1 mL every 30 minutes of a solution containing 5 mg/mL of Levodopa—or half the amounts of a solution containing 10 mg/mL Levodopa.
c. A positive response is seen as an effect on clinical symptoms.
d. A test for determining the plasma concentration of Levodopa is taken (see e.g. Ref. 11, 13, 14 or 15) and this value can be used for establishing the therapeutic threshold value.
e. The infusion velocity is increased further until side effects are noticed.
f. A new plasma concentration value is taken, and the interval between therapeutic threshold value and side effect value is called therapeutic interval.

The magnitude of the therapeutic interval can be used for diagnostic purposes, and for evaluating any previously given Levodopa therapy.

Thus, intravenous Levodopa test is suitable for
1) de novo patients with suspected PD,
2) for evaluating dose regimen in already diagnosed patients,
3) for diagnostic test in patients where the PD diagnosis is disputable,
4) for test of patients evaluated for Deep Brain Stimulation (DBS)-operations.

Preliminary Results
Continuous Infusion of Levodopa

Continuous infusion of Levodopa has been given to PD patients during 12 hours a day for 10 days. The daily dosage of Levodopa was 608 mg and the infusion rate was 51 mg/h. Fifty % of the patients received traditional oral administration of Carbidopa and 50% received Benserazide.

A preliminary compilation of results from seventeen patients has shown a pronounced decrease in clinical fluctuations of the patients with alternating dyskineasia and bradykinesia. This has given the patients a clearly improved quality of life with increased self-sufficiency for several months after the treatment period. The preliminary results can be illustrated by the following case:

A 65 year old woman who had had Parkinson's disease for 20 years with very grave dyskinesia, which disabled her totally for five hours a day, was admitted. Between the dyskinetic periods she was also troubled by severe bradykinesia for a total of seven hours per day. The patient was, during both these conditions, totally dependent on help with hygiene, dressing and feeding. During the greater part of the day she was in a wheel chair apart from one hour in the morning when she could move about with the help of a Zimmerframe. During the infusion treatment the dyskinesia disappeared almost completely and was seen only on very rare occasions when attempts to increase the rate of infusion were made. Some rigidity remained during the entire period of infusion but was not completely disabling. The patient partially needed help with hygiene and dressing but ate by herself and walked with the Zimmerframe. At follow-up six months later the patient could walk without any means of assistance indoors, but used the wheel chair outdoors for reasons of self-confidence. She managed dressing and hygiene herself and could even manage lighter household chores. The patient had, at the checkup, some remaining rigidity but accepted this as it was not disabling. She had not suffered from dyskinesia since the infusion.

The other patients showed, as did the patient described above, a clear improvement in the symptoms of Parkinson's disease during and after the treatment with continuous intravenous Levodopa. Individual variations did occur and this pilot study is not comprehensive enough to securely assess the length of the effect of treatment. The preliminary results did, however, indicate a distinctly improved clinical picture during approximately six months. A greater number of patients must, however, be treated before reliable conclusions can be drawn. The results from the analysis of Levodopa in plasma showed a widening of the therapeutic interval but even here there was not a uniform distribution in the material. The study showed that treatment with intravenous infusion of Levodopa lowered the required oral dosages during the subsequent course of treatment. The calculated mean values of the test group of seventeen patients gave a pre-treatment dosage of 1003 mg/day and a post-treatment dosage of 773 mg/day. The combination of oral Levodopa in standard and in sustained release preparation had even been tried out by several patients before the infusion treatment, but without effect. The infusion also eliminated the rapid shifts from severe dyskinesia to total akinesia. The long-term effect was stable at follow-up 6-10 months after the concluded infusion. Last, but not least, the treatment brings about a greatly improved quality of life.

Intravenous Levodopa Treatment in Intensive Care Units and in Surgery

Patients with PD undergoing surgical operation or patients with critical illnesses treated in intensive care units are often not suitable for oral medication. Intravenous treatment with Levodopa makes it possible to ascertain these patients a normal motor function and more effective and faster mobilisation. Patients with PD are sometimes considered not to be suitable for surgery, because of postoperative rehabilitation difficulties. Peroperative intravenous Levodopa treatment increases the therapeutic possibilities in these cases.

Subcutaneous Infusion

Tests have been made with subcutaneous infusion. They showed a fast distribution of Levodopa to the blood with measurable concentrations and a positive clinical effect for the patient.

One patient has been treated subcutaneously, with continuous infusion of Levodopa, for 3 consecutive days. This resulted in a good clinical effect and measurable blood concentrations of Levodopa in bloodsamples taken once every hour.

The patient was further treated intravenously another day, with continuous Levodopa infusion.

The patient responded in a dose dependant manner on the subcutaneous infusions, but some fluctuations of the Levodopa blood concentrations occurred during the day of the intravenous infusions.

REFERENCES

1. Ehringer H, Hornykiewics O. Verteilung von Noradrenalin und Dopamin (4 hydroxytyramin) im Gehirn des Menchen und ihr Verhalten bei Erkrankungen des extrapyramidalen Systems. Klin Wschr 1960; 38; 1236-39.
2. McGeer P L, McGeer E G, Wads J A. Distribution of tyrosine hydroxylase in human and animal brain. J Neurochem 1971; 18: 1647.

3. The Scientific Basis for the Treatment of Parkinson's Disease 1992. Chapt 7; 114. Ed. Olanow C W and Lieberman A N.
4. Sweet R D and McDowell F H. Plasma dopa concentrations and the 'on-off' effect after chronic treatment of Parkinson's disease. Neurology 1974; 24: 953-6.
5. Caine D, Karoum F, Ruthven C and Sandler M. The metabolism of orally administered Levodopa in parkinsonism. Br J Pharmacol 1969; 37: 57-68.
6. Andersson I, Granerus A-K, Jagenburg R and Svanborg A. Intestinal decarboxylation of orally administered Levodopa. Acta Med Scand 1975; 198: 415-20.
7. Wade D. N, Mearrick B.T and Morris J. Active transport of Levodopa in the intestine. Nature 1973; 242: 463-5.
8. Sasahara K, Nitani T, Habara T, Kojima T, Kawahara Y, Morioka T and Hakajima E. Dosage form design for improvement of bioavailability of levodopa. V. Absorption and metabolism of levodopa in intestinal segments of dogs. J Pharm Sci 1981; 70: 1157-60.
9. Kuruma I, Bartholini G, Tissot R and Pletcher A. The metabolism of L-3-O-metyldopa, a precursor of dopa in man. Clin Pharmacol Therap 1971; 12: 678-82.
10. Messiha F, Hsu T and Bianchine J. Peripheral aromatic L-aminoacids decarboxylase inhibitor in parkinsonism. I. Effect on O-methylated meta-bolites of 1-2-14C-dopa. J Clin Invest 1972; 51: 452-5.
11. Dizdar N, Henriksson A and Kågedal B: Determination of L-3,4-dihydroxyphenylalanine in biological fluids and tissues. J Chromatography 1991; 565: 1-26.
12. Shoulson I, Glaubiger G A and Chase T N. 'On-off' response: clinical and biochemical correlations during oral and intravenous levodopa administration in parkinsonian patients. Neurology 1975; 25: 1144-8.
13. Dizdar N, Kullman A, Norlander B, Olsson J-E, and Kågedal B. Human pharmacokinetics of L-dopa studied with microdialysis. Clin Chem 1999; 45 (10): 1813-1820.
14. Dizdar N, Kullman A, Norlander B, Olsson J-E, and Kågedal B. L-Dopa pharma cokinetics studied with microdialysis in patients with Parkinson's disease and a history of malignant melanoma. Acta Neurol Scand 1999; 100 (4): 231-237.
15. Dizdar N, Årstrand K, and Kågedal B. Analysis of L-dopa in human serum. BioTechniques 2002; 33 (5): 1000-1004.

The invention claimed is:

1. A stable and therapeutically acceptable infusion or injection solution of Levodopa comprising:
   a) at least 10 mg/mL of Levodopa,
   b) an organic buffer,
   c) a physiologically acceptable sugar, and
   d) a physiologically acceptable acid,
   wherein the pH of the solution is lower than or equal to 6, and wherein the solution is prepared by:
   (i) dissolving the Levodopa in the physiologically acceptable acid,
   (ii) adding the organic buffer to the solution of step (i); and
   (iii) adding the physiologically acceptable sugar to the solution of step (ii) in multiple individual portions.

2. The solution of claim 1, having a pH of 3 to 6.

3. The solution of claim 1, comprising 10 mg/ml of Levodopa and having a pH of 3.5 to 4.

4. The solution of claim 1, comprising 10 mg/ml of Levodopa and further comprising at least 0.5 mg/ml of L-2-hydrazino-3-(3,4-dihydroxyphenyl)-2-methylpropanoic acid (Carbidopa) and having a pH of 3.5 to 4.

5. The solution of claim 1, comprising 10 mg/ml of Levodopa and 1 mg/ml of L-2-hydrazino-3-(3,4-dihydroxyphenyl)-2-methylpropanoic acid (Carbidopa) and having a pH of 3.5 to 4.

6. The solution of claim 1, further comprising a stabilizer.

7. The solution of claim 1, wherein the physiologically acceptable acid is hydrochloric acid or acetic acid.

8. A container comprising a volume of the solution of claim 1 adapted for a single or continuous intravenous and/or subcutaneous and/or intrathekal administration.

9. A disposable syringe containing a therapeutically effective amount of an infusion or injection solution of Levodopa according to claim 1.

10. An infusion pump cassette containing a therapeutically effective amount of an infusion or injection solution of Levodopa according to claim 1.

11. A method of preparing a stable and therapeutically acceptable infusion or injection solution of Levodopa comprising:
   a) at least 10 mg/mL of Levodopa,
   b) an organic buffer,
   c) a physiologically acceptable sugar, and
   d) a physiologically acceptable acid,
   wherein the pH of the solution is lower than or equal to 6, wherein the method comprises the steps of:
   (i) dissolving the Levodopa in the physiologically acceptable acid,
   (ii) adding the organic buffer to the solution of step (i); and
   (iii) adding the physiologically acceptable sugar to the solution of step (ii) in multiple individual portions.

12. The method according to claim 11, wherein step (iii) comprises initially adding approximately half the volume of the physiologically acceptable sugar in a solution, followed by a drop by drop addition of the remaining volume of the physiologically acceptable sugar solution during constant stirring.

13. The method according to claim 12, comprising adding the physiologically acceptable sugar solution drop by drop at approximately 10 minute intervals.

14. The method according to claim 13, comprising adding the physiologically acceptable sugar solution until the pH of the solution in step (iii) is in the range of 3 to 6.

15. The method according to claim 11, comprising adjusting the pH of the solution of step (iii) to a value in the range of 3 to 6.

16. The method according claim 11, wherein the solution of step (i) comprises 100 mg/ml of Levodopa, and wherein step (iii) comprises slowly adding a solution of physiologically acceptable sugar in portions of 10 ml.

17. The method of claim 11, wherein the physiologically acceptable sugar is selected from the group consisting of dextran, glucose and mannitol.

18. The method according to claim 17, wherein the solution of step (i) comprises 50 mg/ml of Levodopa and 5 mg/ml of the DDC-inhibitor L-2-hydrazino-3-(3,4-dihydroxyphenyl)-2-methylpropanoic acid (Carbidopa), and wherein step (iii) comprises slowly adding a solution of glucose in portions of 10 ml.

19. The method according to claim 18, wherein the solution of glucose comprises 50 mg/ml of glucose, and wherein the solution of step (iii) comprises 10 mg/ml of Levodopa and 1 mg/ml of Carbidopa having a pH of 3.5 to 4.

20. The method according to claim 11, wherein the infusion or injection solution further comprises a stabilizer.

21. The method according to claim 11, wherein the physiologically acceptable acid is hydrochloric acid or acetic acid.

22. The method according to claim 17, wherein the glucose is added in a solution having a concentration of 50 mg/ml.

23. The solution of claim 1, wherein the physiologically acceptable sugar is selected from the group consisting of dextran, glucose and mannitol.

24. The solution of claim 23, wherein the physiologically acceptable sugar is glucose and the solution has a shelf life exceeding 3 days.

25. The solution of claim 24, having a pH of 3 to 6.

26. The solution of claim 1, further comprising at least 0.5 mg/ml of L-2-hydrazino-3-(3,4-dihydroxyphenyl)-2-methylpropanoic acid (Carbidopa).

27. The solution of claim 24, comprising 10 mg/ml of Levodopa and 1 mg/ml of L-2-hydrazino-3-(3,4-dihydroxyphenyl)-2-methylpropanoic acid (Carbidopa) and having a pH of 3.5 to 4.

28. The method according to claim 17, wherein a solution of glucose comprises 50 mg/ml of glucose and is added to prepare a solution comprising 10 mg/ml of Levodopa having a pH of 3.5 to 4.

29. The method of claim 11, wherein the physiologically acceptable sugar is glucose and the solution has a shelf life exceeding 3 days.

\* \* \* \* \*